(12) United States Patent
Darbandi et al.

(10) Patent No.: US 12,156,962 B2
(45) Date of Patent: Dec. 3, 2024

(54) FILTERING CASSETTES AND FILTERING SYSTEMS

(71) Applicant: MINNETRONIX NEURO, INC., St. Paul, MN (US)

(72) Inventors: Bejan Michael Darbandi, Chanhassen, MN (US); Aaron R. Mccabe, Edina, MN (US); Justin Charles Jones, Minneapolis, MN (US)

(73) Assignee: MINNETRONIX NEURO, INC., St. Paul, MN (US)

( * ) Notice: Subject to any disclaimer, the term of this patent is extended or adjusted under 35 U.S.C. 154(b) by 623 days.

(21) Appl. No.: 17/316,311

(22) Filed: May 10, 2021

(65) Prior Publication Data
US 2021/0346588 A1 Nov. 11, 2021

Related U.S. Application Data

(60) Provisional application No. 63/022,733, filed on May 11, 2020.

(51) Int. Cl.
*A61M 1/00* (2006.01)

(52) U.S. Cl.
CPC ....... *A61M 1/72* (2021.05); *A61M 2202/0464* (2013.01); *A61M 2205/125* (2013.01); *A61M 2206/16* (2013.01)

(58) Field of Classification Search
CPC ............ A61M 1/00; A61M 1/72; A61M 1/88; A61M 2202/0464; A61M 2205/125; A61M 2205/6045; A61M 2206/16; A61M 27/006; A61M 27/00; A61M 2027/004; A61M 25/00; A61M 25/003
(Continued)

(56) References Cited

U.S. PATENT DOCUMENTS

| 4,904,237 A | 2/1990 | Janese |
| 5,334,315 A | 8/1994 | Matkovich et al. |

(Continued)

FOREIGN PATENT DOCUMENTS

| JP | 2003515394 A | 5/2003 |
| JP | 2006175232 A | 7/2006 |

(Continued)

OTHER PUBLICATIONS

Invitation to Pay Additional Fees dated Jan. 17, 2019 for International Application No. PCT/US2018/054478.

(Continued)

*Primary Examiner* — Akash K Varma
(74) *Attorney, Agent, or Firm* — Seager, Tufte & Wickhem LLP (57) ABSTRACT

Filtering cassettes, filtering systems, and methods for using the same are disclosed. An example filtering cassette may include a cassette housing. An inlet may be coupled to the cassette housing. The inlet may be configured to receive cerebrospinal fluid from a catheter. An outlet may be coupled to the cassette housing. The outlet may be configured to direct filtered cerebrospinal fluid to the catheter. One or more filters may be disposed within the cassette housing. An arcuate surface may be defined along a periphery of the cassette housing. The arcuate surface may be configured to engage a controller assembly when the cassette housing is mounted to the controller assembly.

8 Claims, 5 Drawing Sheets

(58) Field of Classification Search
USPC ........................................................ 210/600
See application file for complete search history.

(56) References Cited

U.S. PATENT DOCUMENTS

| | | | |
|---|---|---|---|
| 5,897,528 | A | 4/1999 | Schultz |
| 5,980,480 | A | 11/1999 | Rubenstein et al. |
| 6,013,051 | A | 1/2000 | Nelson |
| 6,139,517 | A | 10/2000 | Macoviak et al. |
| 6,217,552 | B1 | 4/2001 | Barbut et al. |
| 6,379,331 | B2 | 4/2002 | Barbut et al. |
| 6,383,159 | B1 | 5/2002 | Saul et al. |
| 6,558,412 | B2 | 5/2003 | Dobak, III |
| 6,575,928 | B2 | 6/2003 | Saul et al. |
| 6,623,514 | B1 | 9/2003 | Chin |
| 6,682,508 | B1 | 1/2004 | Meythaler et al. |
| 6,689,085 | B1 | 2/2004 | Rubenstein et al. |
| 6,758,832 | B2 | 7/2004 | Barbut et al. |
| 6,875,192 | B1 | 4/2005 | Saul et al. |
| 6,905,474 | B2 | 6/2005 | Borgesen |
| 6,972,028 | B2 | 12/2005 | Chin |
| 7,014,624 | B2 | 3/2006 | Meythaler et al. |
| 7,025,739 | B2 | 4/2006 | Saul |
| 7,025,742 | B2 | 4/2006 | Rubenstein et al. |
| 7,150,737 | B2 | 12/2006 | Purdy et al. |
| 7,156,867 | B2 | 1/2007 | Lennox |
| 7,189,221 | B2 | 3/2007 | Silverberg et al. |
| 7,241,307 | B2 | 7/2007 | Lennox |
| 7,309,330 | B2 | 12/2007 | Bertrand et al. |
| 7,695,627 | B2 | 4/2010 | Bosch et al. |
| 7,715,896 | B2 | 5/2010 | Ramzipoor et al. |
| 7,787,954 | B2 | 8/2010 | Purdy |
| 7,887,503 | B2 | 2/2011 | Geiger |
| 7,976,517 | B2 | 7/2011 | Dextradeur et al. |
| 8,131,353 | B2 | 3/2012 | Purdy |
| 8,221,366 | B2 | 7/2012 | Hoffman et al. |
| 8,221,392 | B2 | 7/2012 | Dextradeur et al. |
| 8,292,856 | B2 | 10/2012 | Bertrand et al. |
| 8,398,581 | B2 | 3/2013 | Panotopoulos |
| 8,518,636 | B2 | 8/2013 | Bosch et al. |
| 8,603,057 | B2 | 12/2013 | Hoffman et al. |
| 8,608,716 | B2 | 12/2013 | Jolper et al. |
| 8,784,845 | B2 | 7/2014 | Bruce et al. |
| 8,827,944 | B2 | 9/2014 | Sevrain |
| 9,011,368 | B2 | 4/2015 | Rivera-Begeman |
| 9,205,184 | B2 | 12/2015 | Eckermann |
| 9,295,821 | B2 | 3/2016 | Miethke et al. |
| 9,345,826 | B2 | 5/2016 | Kenley et al. |
| 9,387,311 | B1 | 7/2016 | Heilman et al. |
| 9,421,348 | B2 | 8/2016 | Lenihan et al. |
| 9,498,605 | B2 | 11/2016 | Fifolt et al. |
| 9,623,177 | B2 | 4/2017 | Panotopoulos |
| 9,656,015 | B2 | 5/2017 | Bruce et al. |
| 9,662,479 | B2 | 5/2017 | Heilman et al. |
| 9,669,195 | B2 | 6/2017 | Heilman et al. |
| 9,694,166 | B2 | 7/2017 | Hurt |
| 9,717,890 | B2 | 8/2017 | Holper et al. |
| 9,724,501 | B2 | 8/2017 | Heilman et al. |
| 9,731,101 | B2 | 8/2017 | Bertrand et al. |
| 9,919,138 | B2 | 3/2018 | Enihan et al. |
| 10,058,686 | B2 | 8/2018 | Heilman et al. |
| 10,174,361 | B2 | 1/2019 | Skog et al. |
| 2002/0193285 | A1 | 12/2002 | Hesson et al. |
| 2003/0130651 | A1 | 7/2003 | Lennox |
| 2003/0220675 | A1 | 11/2003 | Coin |
| 2004/0068201 | A1 | 4/2004 | Saul |
| 2004/0092908 | A1 | 5/2004 | Harper et al. |
| 2004/0092909 | A1 | 5/2004 | Harper et al. |
| 2004/0092910 | A1 | 5/2004 | Harper et al. |
| 2005/0090775 | A1 | 4/2005 | Harper et al. |
| 2005/0256510 | A1 | 11/2005 | Moskowitz et al. |
| 2006/0184098 | A1 | 8/2006 | Barnitz et al. |
| 2007/0112291 | A1 | 5/2007 | Borgesen |
| 2007/0112293 | A1 | 5/2007 | Borgesen |
| 2007/0135778 | A1* | 6/2007 | Murray ................ A61B 50/36 604/317 |
| 2007/0246406 | A1 | 10/2007 | Dibel et al. |
| 2008/0195024 | A1 | 8/2008 | Schmid-Schonbein et al. |
| 2008/0249501 | A1 | 10/2008 | Yamasaki |
| 2009/0012460 | A1 | 1/2009 | Steck et al. |
| 2009/0131857 | A1 | 5/2009 | Geiger |
| 2009/0186065 | A1 | 7/2009 | Tillman et al. |
| 2010/0030196 | A1 | 2/2010 | Hildebrand et al. |
| 2010/0305492 | A1* | 12/2010 | Lad ................. A61M 25/0026 604/9 |
| 2011/0033463 | A1 | 2/2011 | Thakker et al. |
| 2011/0046547 | A1 | 2/2011 | Mantle |
| 2011/0098623 | A1 | 4/2011 | Zhang et al. |
| 2012/0156716 | A1 | 6/2012 | Walsh et al. |
| 2012/0211367 | A1 | 8/2012 | Vecitis |
| 2013/0023814 | A1 | 1/2013 | Bertrand et al. |
| 2013/0052647 | A1 | 2/2013 | Goldrick et al. |
| 2013/0158470 | A1 | 6/2013 | Panotopoulos |
| 2013/0248450 | A1 | 9/2013 | Kenley et al. |
| 2014/0037656 | A1 | 2/2014 | Felder |
| 2014/0166555 | A1 | 6/2014 | Dibel et al. |
| 2015/0076047 | A1 | 3/2015 | Cho et al. |
| 2015/0136701 | A1 | 5/2015 | Chait |
| 2015/0157781 | A1 | 6/2015 | Kyle et al. |
| 2015/0273129 | A1 | 10/2015 | Freeman et al. |
| 2016/0136398 | A1 | 5/2016 | Heilman et al. |
| 2016/0263305 | A1 | 9/2016 | Kenley et al. |
| 2016/0303355 | A1 | 10/2016 | Heilman et al. |
| 2017/0035950 | A1 | 2/2017 | Meyering et al. |
| 2017/0216502 | A1 | 8/2017 | Panotopoulos |
| 2017/0304521 | A1 | 10/2017 | McNeil |
| 2018/0312925 | A1 | 11/2018 | Umansky et al. |
| 2019/0009014 | A1 | 1/2019 | Chen et al. |

FOREIGN PATENT DOCUMENTS

| | | | | |
|---|---|---|---|---|
| JP | | 2008006292 A | 1/2008 | |
| JP | | 2010532237 A | 10/2010 | |
| JP | | 2018537191 A | 12/2018 | |
| WO | | 2001039819 A2 | 6/2001 | |
| WO | WO-2010123558 A1 * | | 10/2010 | .......... A61M 27/006 |
| WO | WO-2011114260 A1 * | | 9/2011 | .............. A61F 2/01 |
| WO | WO-2017023419 A1 * | | 2/2017 | .......... A61M 1/0094 |
| WO | | 2017096228 A1 | 6/2017 | |
| WO | | 2020068509 A1 | 4/2020 | |

OTHER PUBLICATIONS

International Search Report and Written Opinion dated Mar. 11, 2019 for International Application No. PCT/US2018/054478.
International Search Report and Written Opinion dated Oct. 5, 2021 for International Application No. PCT/US2021/038198.

* cited by examiner

FILTERING CASSETTES AND FILTERING SYSTEMS

CROSS-REFERENCED TO RELATED APPLICATIONS

The present application claims the benefit of and priority to U.S. Provisional Patent Application Ser. No. 63/022,733, filed on May 11, 2020, the disclosure of which is incorporated herein by reference.

TECHNICAL FIELD

The present disclosure relates to filtering cassettes, filtering systems, and methods for treating along the central nervous system.

BACKGROUND

A wide variety of medical devices have been developed for medical use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. A filtering cassette is disclosed. The filtering cassette comprises: a cassette housing; an inlet coupled to the cassette housing, the inlet being configured to receive cerebrospinal fluid from a catheter; an outlet coupled to the cassette housing, the outlet being configured to direct filtered cerebrospinal fluid to the catheter; one or more filters disposed within the cassette housing; and an arcuate surface defined along a periphery of the cassette housing, the arcuate surface being configured to engage a controller assembly when the cassette housing is mounted to the controller assembly.

Alternatively or additionally to any of the embodiments above, further comprising a cover coupled to the cassette housing.

Alternatively or additionally to any of the embodiments above, the cover includes one or more flanges.

Alternatively or additionally to any of the embodiments above, the cover includes a handle member.

Alternatively or additionally to any of the embodiments above, the cassette housing includes a top portion, a bottom portion, and opposing side portions; and wherein the arcuate surface is disposed along a first one of the opposing side portions.

Alternatively or additionally to any of the embodiments above, a second one of the opposing side portions extends substantially linearly between the top portion and the bottom portion.

Alternatively or additionally to any of the embodiments above, the one or more filters includes a tangential flow filter.

Alternatively or additionally to any of the embodiments above, the cassette housing includes a connecting projection.

A filtering system is disclosed. The filtering system comprises: a controller assembly having a cassette socket with an arcuate wall region; a filtering cassette disposed within the cassette socket, the filtering cassette including: a cassette housing, an inlet coupled to the cassette housing, the inlet being configured to receive cerebrospinal fluid from a catheter, an outlet coupled to the cassette housing, the outlet being configured to direct filtered cerebrospinal fluid to the catheter, one or more filters disposed within the cassette housing, and an arcuate surface defined along a periphery of the cassette housing; and wherein the arcuate surface is configured to engage the arcuate wall region when the cassette housing is disposed within the controller assembly.

Alternatively or additionally to any of the embodiments above, further comprising a cover coupled to the cassette housing.

Alternatively or additionally to any of the embodiments above, the cover includes one or more flanges.

Alternatively or additionally to any of the embodiments above, the cover includes a handle member.

Alternatively or additionally to any of the embodiments above, the cassette housing includes a top portion, a bottom portion, and opposing side portions; and wherein the arcuate surface is disposed along a first one of the opposing side portions.

Alternatively or additionally to any of the embodiments above, a second one of the opposing side portions extends substantially linearly between the top portion and the bottom portion.

Alternatively or additionally to any of the embodiments above, the cassette socket includes a linear wall region configured to engage the second one of the opposing side portions.

Alternatively or additionally to any of the embodiments above, the cassette housing includes a connecting projection.

Alternatively or additionally to any of the embodiments above, the cassette socket includes an opening configured to receive the connecting projection.

Alternatively or additionally to any of the embodiments above, the one or more filters includes a tangential flow filter.

A filtering cassette is disclosed. The filtering cassette comprises: a cassette housing including a top portion, a bottom portion, a first side portion, and a second side portion; one or more filters disposed within the cassette housing; an inlet connector coupled to the cassette housing, the inlet connector being configured to receive a fluid from a catheter; an outlet connector coupled to the cassette housing, the outlet connector being configured to return a filtered fluid to the catheter; and wherein the first side portion defines a mounting region that extends along a non-linear path between the top portion and the bottom portion of the cassette housing.

Alternatively or additionally to any of the embodiments above, further comprising a cover coupled to the cassette housing.

Alternatively or additionally to any of the embodiments above, the cover includes one or more flanges.

Alternatively or additionally to any of the embodiments above, the cover includes a handle member.

Alternatively or additionally to any of the embodiments above, the mounting region is arcuate.

Alternatively or additionally to any of the embodiments above, the one or more filters includes a tangential flow filter.

Alternatively or additionally to any of the embodiments above, the cassette housing includes a connecting projection.

A filtering cassette for filtering cerebrospinal fluid is disclosed. The filtering cassette comprises: a cassette housing; an inlet coupled to the cassette housing, the inlet being configured to receive cerebrospinal fluid from a patient; an outlet coupled to the cassette housing, the outlet being configured to direct filtered cerebrospinal fluid to the patient; one or more filters disposed within the cassette housing; and an arcuate surface defined along a periphery of the cassette housing, the arcuate surface being configured to engage a controller assembly when the cassette housing is mounted to the controller assembly.

A filtering system for filtering cerebrospinal fluid is disclosed. The filtering system comprises: a controller assembly having a cassette socket with an arcuate wall region; a filtering cassette disposed within the cassette socket, the filtering cassette including: a cassette housing, an inlet coupled to the cassette housing, the inlet being configured to receive cerebrospinal fluid from a patient, an outlet coupled to the cassette housing, the outlet being configured to direct filtered cerebrospinal fluid to the patient, one or more filters disposed within the cassette housing, and an arcuate surface defined along a periphery of the cassette housing; and wherein the arcuate surface is configured to engage the arcuate wall region when the cassette housing is disposed within the controller assembly.

A filtering cassette is disclosed. The filtering cassette comprises: a cassette housing including a top portion, a bottom portion, a first side portion, and a second side portion; one or more filters disposed within the cassette housing; an inlet connector coupled to the cassette housing, the inlet connector being configured to receive a fluid from a patient; an outlet connector coupled to the cassette housing, the outlet connector being configured to return a filtered fluid to the patient; wherein the first side portion defines a mounting region that extends along a non-linear path between the top portion and the bottom portion of the cassette housing.

A filtering cassette is disclosed. The filtering cassette comprises: a cassette housing; an inlet coupled to the cassette housing, the inlet being configured to receive cerebrospinal fluid from a catheter; an outlet coupled to the cassette housing, the outlet being configured to direct filtered cerebrospinal fluid to the catheter; one or more filters disposed within the cassette housing; and a waste outlet coupled to the cassette housing.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAIL DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Cerebrospinal fluid (CSF) is a generally clear, colorless fluid with viscosity similar to water that is produced within the choroid plexus located in the ventricles of the brain. Total CSF volume has been estimated to range from approximately 150 to 300 milliliters in healthy adults. The choroid plexus is believed to produce approximately 500 milliliters of CSF daily in order to accommodate flushing or recycling of CSF to remove toxins and metabolites. The total volume of CSF is replenished several times per day or possibly more during sleep cycles and other activities. CSF also serves to float the delicate brain tissue by the Archimedes principle, and it protects the brain from sudden movements by cushioning the tissue. From the choroid plexus, CSF flows slowly through a series of openings into the space surrounding the brain and spinal column, and then into the body through multiple outflow pathways that include arachnoid granulations, cribiform plate, dural lymphatics, spinal cord nerve root sleeves, and possibly other pathways within the brain tissue. CSF is found in the space between the pia mater and the arachnoid mater, known as the subarachnoid space and also located within the ventricular system of the brain and in a series of cisterns located external to the brain. In addition to the net production and absorption of CSF flow, the CSF oscillates with a back-and-forth motion in synchrony with the cardiac and respiratory cycle. The magnitude of these oscillations is variable depending on the specific region of CSF. CSF flow can also be intermittently altered based on various maneuvers such as valsalva, coughing, sneezing, playing a musical instrument, and athletic activities. CSF pressure in a healthy adult is approximately 10 millimeters of mercury in the supine position. CSF pressure is altered in the standing position by hydrostatic pressure gradient along CSF system and can also be transiently affected by maneuvers such as coughing.

Research has indicated that alterations of the biochemical composition of CSF can be indicative and/or involved in the pathological processes of a plethora of central nervous system disease states. For example, in the event of a stroke or other brain trauma, blood can enter the CSF system leading to subsequent injury to the brain due to blood clotting and other biological processes. In context of amyotrophic lateral sclerosis, several chemicals (inflammatory proteins or cytokines such as CHIT1) have been found to be abnormally elevated potentially contributing to the disease pathology. Similarly, in multiple sclerosis proteins, cytokines and chemokines have been found to be elevated and potentially underlying disease progression. As such, in principle, it could be beneficial to remove CSF with abnormal biochemical composition; however, direct removal of CSF is limited as only relatively small amounts can be safely removed. Thus, it can be desirable to remove the CSF from one location (e.g., the cervical region of the spine, or a brain ventricle), alter it (e.g., filter), and return it to the CSF space at a second location (e.g., the lumbar region of the spine). This process can be used to remove the unwanted biochemical products while maintaining similar total CSF volume.

A process termed Neurapheresis may be understood to be the modification of materials (e.g. removal of microorganisms, cells, viruses, foreign material, drugs, combinations thereof, and the like, or circulation and/or addition of materials such as pharmacologic agents) from CSF. This and other therapeutic techniques can be used to treat a number of neurological diseases or conditions, such as Alzheimer's Disease, Parkinson's Disease, Huntington's Disease, Amyotrophic Lateral Sclerosis (ALS), Encephalitis from various causes, Meningitis from various causes, Guillain-Barré Syndrome (GBS), Multiple Sclerosis (MS), HIV-associated neurocognitive disorders, Spinal Cord Injury, Traumatic Brain Injury, cerebral vasospasm, stroke and other diseases or conditions. In addition, a filtering process or system (e.g., a Neurapheresis process or system) can be used during open or endoscopic spine surgery or brain surgery, for example to remove blood that may get in the CSF during the surgery.

Figure 1:
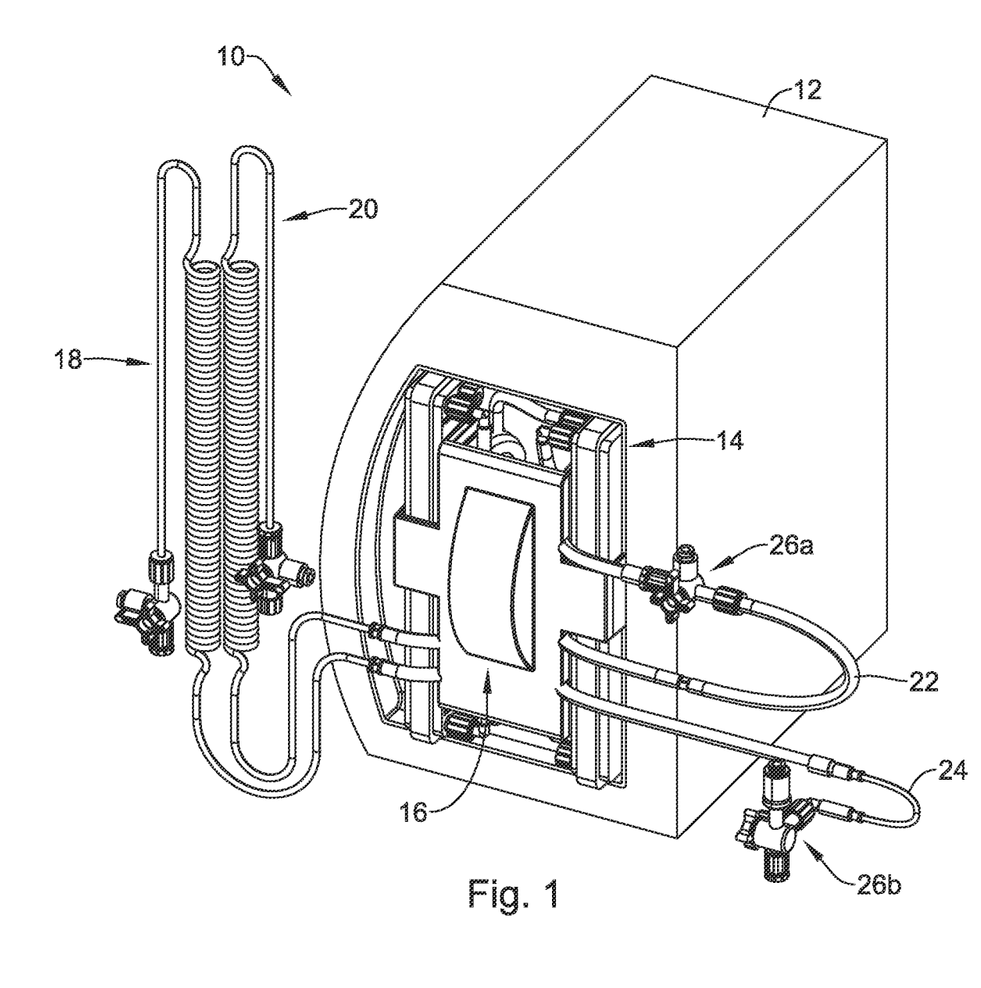
FIG. 1 illustrates an example filtering system.

FIG. 1 illustrates an example filtering system 10, for example a Neurapheresis filtering system 10. The system 10 may include a controller assembly 12 and a filtering cassette 16. In at least some instances, the controller assembly 12 may be considered capital equipment for a hospital and/or clinic. In other words, the controller assembly 12 is designed for repeated/multiple uses and/or designed for repeated/multiple interventions and/or designed for repeated/multiple patients. In some of these and in other instances, the filtering cassette 16 may be considered to be a single-use product. Thus, the filtering cassette 16 may be designed to be mounted/coupled to controller assembly 12 for a given intervention, used for the intervention, and then removed from the controller assembly 12 when the intervention is completed. The controller assembly 12 can be re-used in a subsequent intervention by mounting/coupling a new filtering cassette 16 thereto. In order to efficiently accommodate the mounting/coupling and/or removing of filtering cassette(s) (e.g., like the filtering cassette 16) thereto, the controller assembly 12 may include a mounting region or socket 14 that is designed to mate with and/or otherwise accommodate the filtering cassette 16. The socket 14, along with the corresponding shaped surfaces/housing of the filtering cassette 16 (e.g., which is described in more detail herein), helps to make mounting/coupling and/or removing the filtering cassette 16 a relatively straightforward procedure for a clinician.

In at least some instances, the filtering cassette 16 includes one or more filters (e.g., such as tangential flow filters, dead-end filters, electrofilters, combinations thereof, and/or the like) generally designed to filter CSF. Tubing may be coupled to the filtering cassette 16. In some instances, the tubing may include an aspiration or inlet region 18 that may be coupled to the filtering cassette 16. The inlet region 18 may be coupled to a catheter (not shown) and may define a pathway through which CSF can be removed from a patient and be processed/filtered by the filtering cassette 16. In some instances, the tubing may include a return or outlet region 20 that may be coupled to the filtering cassette 16. The return region 20 may be used to return CSF (e.g., filtered CSF) to the patient. The return region 20 may be coupled to a catheter (not shown) and may define a pathway through which processed/filtered CSF can be returned to the patient.

The tubing coupled to the filtering cassette 16 may also include a first pump region 22, for example, that may extend from the filtering cassette 16. The first pump region 22 may be designed to engage a pump head (not shown) so that CSF can be pumped/circulated through the filtering cassette 16 and, ultimately filtered CSF can be returned to the patient. The tubing coupled to the filtering cassette 16 may include a second pump region 24, for example, that may extend from the filtering cassette 16. The second pump region 24 may be designed to engage another pump head (not shown) so that waste material can be pumped from the filtering cassette 16.

In use, the system 10 may be used by coupling a catheter (not shown) to the system 10 and disposing the catheter within/along the cerebrospinal space (e.g., such as along lumbar cerebrospinal space). CSF may be removed/aspirated using the catheter and the removed CSF may be processed/filtered using the filtering cassette 16. The filtered/conditioned CSF may then be returned to the patient using the catheter.

The tubing may include one or more sampling ports, for example sampling ports 26a, 26b, generally disposed along the tubing of the filtering cassette 16. It can be appreciated that the position of a given sampling port may impact the type of CSF sample collected. For example, sampling port 26a may be disposed adjacent to the filtering cassette 16 and be in fluid communication with the inlet region 18 such that samples collected at the sampling port 26a represent CSF collected directly from the patient (e.g., "unfiltered" or "untreated" CSF). Samples collected at the sampling port 26a, thus, may be used to analyze the CSF, quantify one or more substances (e.g., pathogens, prokaryotic organisms, eukaryotic organisms, viruses, contaminants, drugs, and/or the like) within the CSF, monitor drug levels in the CSF, monitor progress of a treatment, combinations thereof, and/or the like. The sampling port 26b may be disposed adjacent to the filtering cassette 16 such that waste material (e.g., material removed/filtered from CSF) can be collected and/or analyzed. Thus, the sampling port 26b may be understood to be in fluid communication with a waste outlet (e.g., a pathway from the filtering cassette 16 where the waste material is transported). The system 10 may include additional ports that allow for a clinician to assess the filtration during a Neurapheresis procedure. Such sampling ports may be disposed along or in fluid communication with the return region 20. For example, one or more additional sampling ports may be in fluid communication with the return region 20 such that samples collected at this sampling port represent filtered/treated CSF. One or more additional sampling ports may be in fluid communication with the inlet region 18 such that samples collected at this sampling port represent unfiltered CSF. Thus, collectively, sampling ports are contemplated that can be used to collect (a) unfiltered CSF, (b) filtered/treated CSF, and/or (c) waste material.

Figure 2:
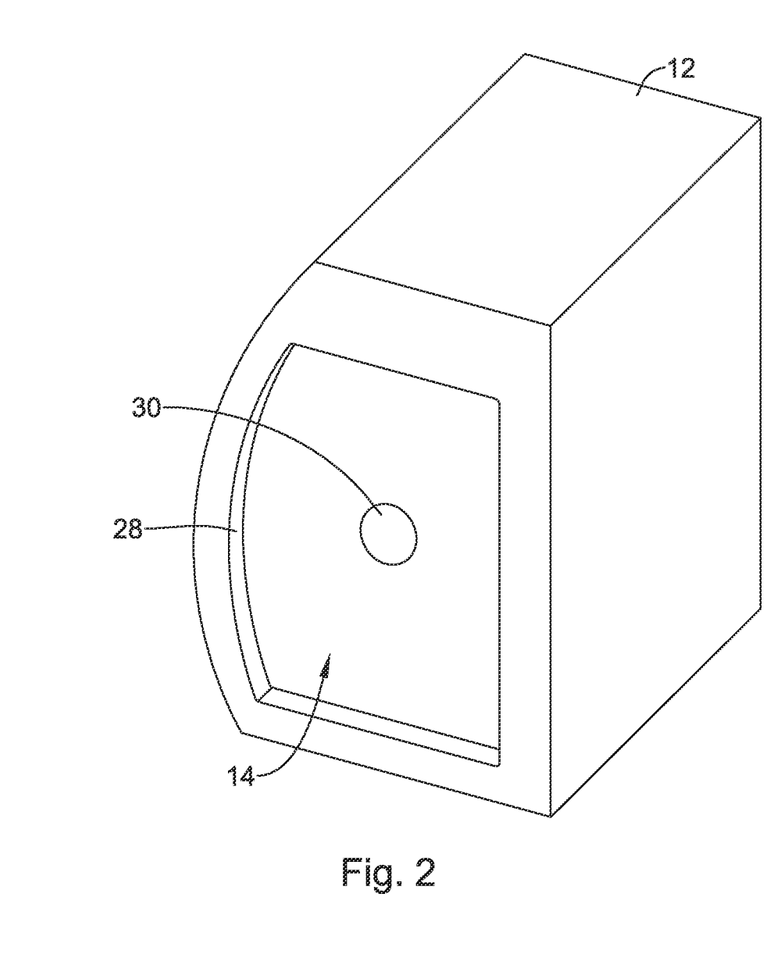
FIG. 2 illustrates an example controller assembly.

FIG. 2 illustrates the controller assembly 12 without the filtering cassette 16. The view depicted in FIG. 2 may be understood to be a side view, with the front of the controller assembly 12 (e.g., which may include one or more inputs/buttons, one or more displays, etc.) not being fully shown/seen. From this side view, the socket 14 for receiving the filtering cassette 16 can be seen. It can be appreciated that the socket 14 may be positioned at any suitable location on the controller assembly 12 (e.g., the top, rear, opposite side, front, etc.). In at least some instances, the socket 14 may include an arcuate wall surface 28. The arcuate wall surface 28 may be shaped to match a corresponding surface on the filtering cassette 16 (e.g., an arcuate surface of the filtering cassette 16 as described herein). In addition, the socket 14 may include an opening 30. The opening 30 may include a connector that allows an object (e.g., such as the filtering cassette 16) engaging the opening 30 to connect with (e.g., electrically connect) with the controller assembly 12.

Figure 3:
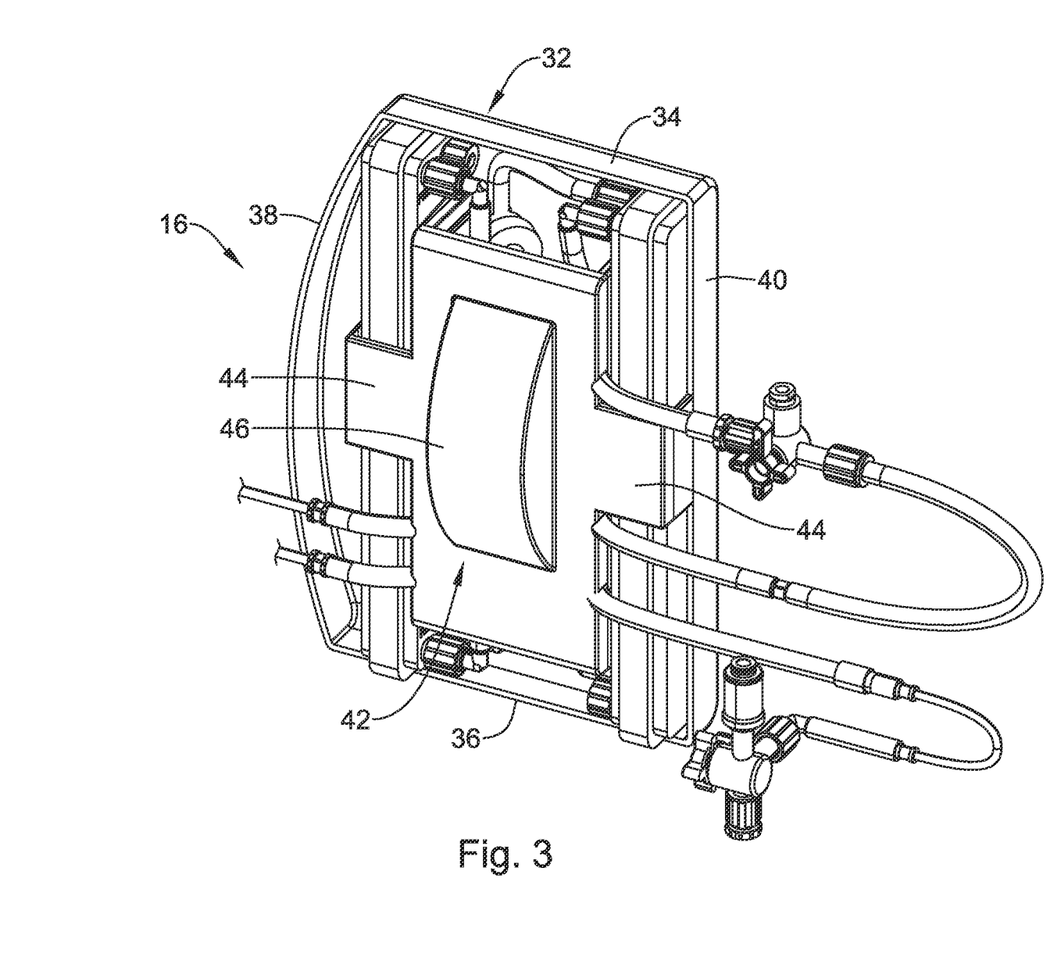
FIG. 3 illustrates an example filtering cassette.

FIG. 3 illustrates the filtering cassette 16. Here it can be seen that the filtering cassette 16 includes a cassette housing 32. The cassette housing 32 may include a top portion 34, a bottom portion 36, a first side portion 38, and a second side portion 40. In at least some instances, the first side portion 38 extends in a non-linear manner between the top portion 34 and the bottom portion 36. Thus, the first side portion 38 may be understood to be a non-linear or non-vertical surface, for example an arcuate surface. The arcuate first side portion 38 is generally designed to engage or otherwise correspond with the arcuate wall surface 28 of the controller assembly 12. In at least some instances, the opposing second side portion 40 extends in a linear manner directly between the top portion 34 and the bottom portion 36. In other words, the second side portion 40 may be understood to be a linear or vertical surface. This combination of the arcuate first side portion 38 and the linear/vertical second side portion 40 may give the cassette housing 32 an at least partially asymmetric shape. Thus, engagement of the filtering cassette 16 with the controller assembly 12 can be efficiently achieved.

The filtering cassette 16 may also include a cover 42. The cover 42 may include one or more flanges or flanged regions 44. The cover 42 may include a handle or handle member 46. The handle 46 may aid a user in securing the filtering cassette 16 with the controller assembly 12. In some instances, the cover 42 may be removable from the cassette housing 32. In other instances, the cover 42 may be substantially secured/fixed to the cassette housing 32. The filtering cassette 16 and/or the controller assembly 12 may include one or more structural features to help secure the filtering cassette 16 with the controller assembly 12. This may include regions on the handle 46 or other portions of the filtering cassette that are designed to engage a lipped surface on the controller assembly 12. In some instances, one or more electrical connectors may disposed along the filtering cassette 16 and/or the controller assembly 12. For example, the electrical connectors may be disposed along portions 36/36/38/40 of the filtering cassette 16. Alternatively, the filtering cassette 16 may include a flange or projection designed to interface or engage a corresponding socket along the controller assembly 12. An electrical connector may be disposed along the flange and/or along the socket.

Figure 4:
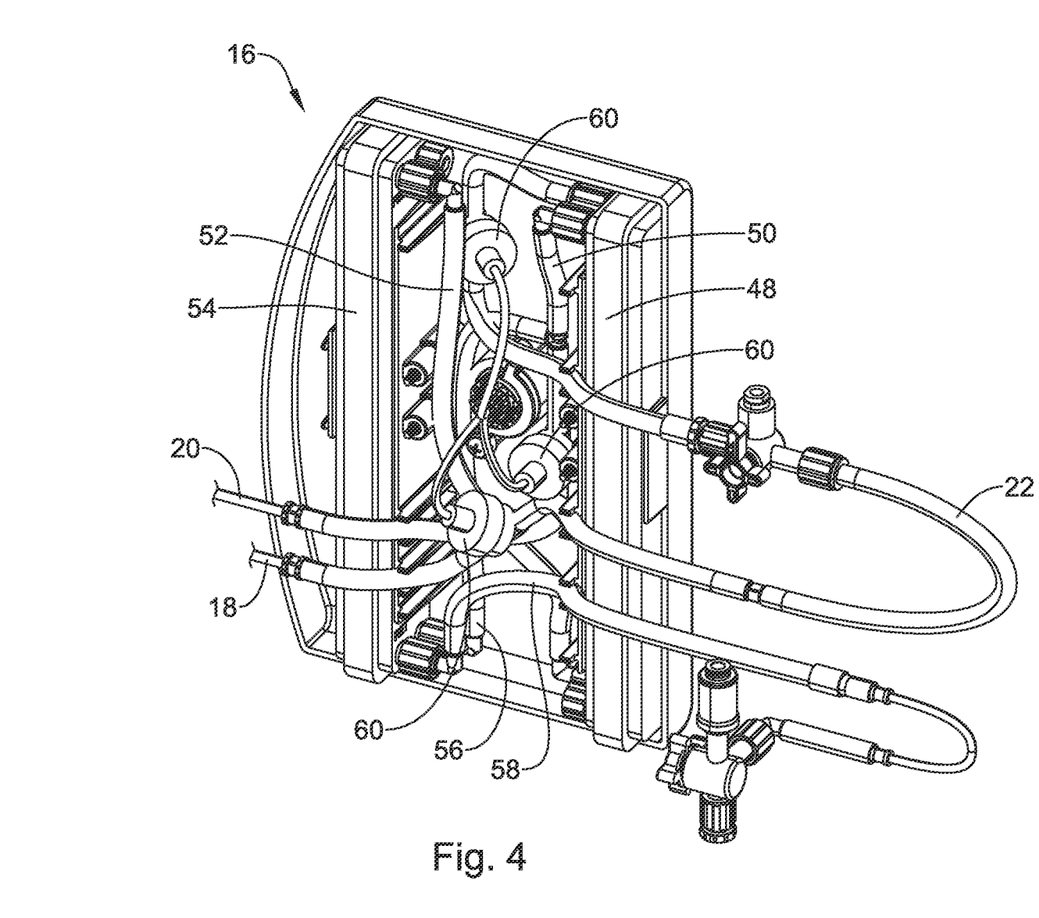
FIG. 4 illustrates an example filtering cassette.

FIG. 4 illustrates the filtering cassette 16 with the cover 42 removed. Here, the fluid pathways through the filtering cassette 16 can be seen. For example, fluid may travel from the catheter (not shown) to/along the inlet region 18, toward the first pump region 22, and to a first filter 48. In some instances, the fluid is cerebrospinal fluid removed from a patient with the catheter. The first filter 48 may separate the fluid into a filtrate and a retentate. When the fluid is cerebrospinal fluid, the filtrate may be understood to be filtered or conditioned cerebrospinal fluid. The filtrate may advance along a filtrate pathway 50 toward the outlet region 20 (e.g., where the fluid may be returned to the patient). The retentate may be further filtered. As such, the retentate may advance along a retentate pathway 52 to a second filter 54. The filtrate from the second filter 54 may advance along a second filtrate pathway 56 and merge with the filtrate pathway 50, and then advance toward the outlet region 20 (e.g., along with fluid traveling along the filtrate pathway 50). When the fluid is cerebrospinal fluid, the filtrate from the second filter 54 may be understood to be filtered or conditioned cerebrospinal fluid. The retentate from the second filter 54 (e.g., the waste) may advance along a second retentate pathway 58 toward the second pump region 24.

Also shown in FIG. 4 is that the filtering cassette 16 may include one or more sensors 60. The sensors 60 may be used to measure flow through, volume through, and/or pressure within the filtering cassette 16 so that proper flow through the filtering cassette 16 can be maintained. In some instances, the filtering cassette 16 may include one or more pumps (e.g., in-line pumps) or pumping mechanisms (not shown) therein.

Figure 5:
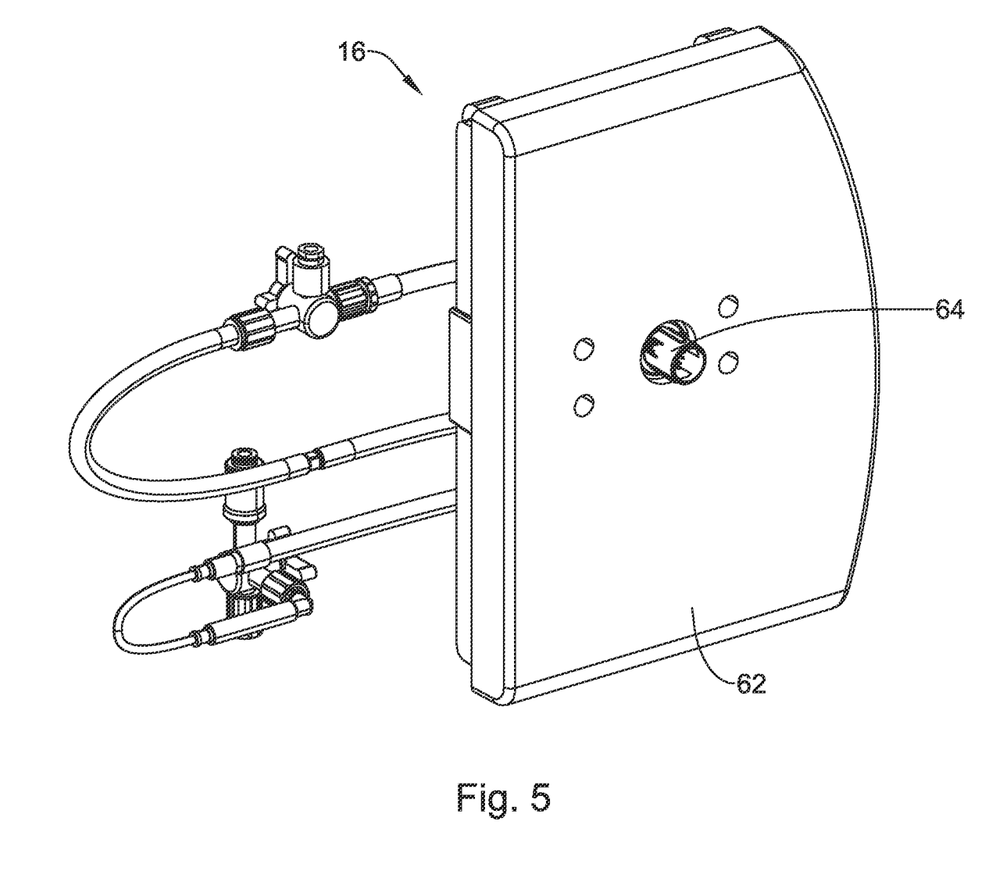
FIG. 5 illustrates an example filtering cassette.

FIG. 5 illustrates a rear surface 62 of the filtering cassette 16. Here it can be seen that the filtering cassette 16 may include a projection 64. The projection 64 may include a connector and/or one or more electrical contacts. The projection 64 generally is configured to fit within or otherwise engage the opening 30 within the socket 14 of the controller assembly 12. In some instances, the projection 64 may allow information from the sensors 60 to be transmitted to/from the controller assembly 12.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A removable filtering cassette, comprising:
   a cassette housing;
   a tubing coupled to the cassette housing, the tubing including an inlet region and an outlet region, wherein:
      the inlet region is coupled to the cassette housing and is configured to receive cerebrospinal fluid from a catheter disposed within a cerebrospinal space of a patient;
      the outlet region coupled to the cassette housing and is configured to direct filtered cerebrospinal fluid to the catheter through which the filtered cerebrospinal fluid can be returned to the cerebrospinal space of the patient;
   one or more filters disposed within the cassette housing between the inlet region and the outlet region, wherein the one or more filters are configured to filter the cerebrospinal fluid removed from the cerebrospinal space of the patient;

a connecting projection extending from a rear surface of the cassette housing, the connecting projection including one or more electrical contacts and the connecting projection being configured to engage an opening in a cassette socket in a controller and pump assembly so that the removable filtering cassette can be removably attached to the controller and the pump assembly; and an arcuate side surface defined along a periphery of the cassette housing, the arcuate side surface being shaped to match a corresponding arcuate side surface on the controller and the pump assembly and the arcuate side surface on the cassette housing being configured to removably engage the corresponding arcuate side surface on the controller and the pump assembly when the cassette housing is mounted to the controller and the pump assembly.

2. The removable filtering cassette of claim 1, further comprising a cover coupled to the cassette housing.

3. The removable filtering cassette of claim 2, wherein the cover includes one or more flanges.

4. The removable filtering cassette of claim 2, wherein the cover includes a handle member.

5. The removable filtering cassette of claim 1, wherein the cassette housing includes a top portion, a bottom portion, and opposing side portions; and wherein the arcuate side surface is disposed along a first one of the opposing side portions.

6. The removable filtering cassette of claim 5, wherein a second one of the opposing side portions extends substantially linearly between the top portion and the bottom portion.

7. The removable filtering cassette of claim 1, wherein the one or more filters includes a tangential flow filter.

8. The removable filtering cassette of claim 1, wherein the cassette housing has an asymmetric shape defined at least in part by the arcuate side surface and a linear vertical side surface that is opposite from the arcuate side surface. .

* * * * *